United States Patent [19]
Brinson

[11] Patent Number: 5,797,919
[45] Date of Patent: Aug. 25, 1998

[54] SURGICAL BONE CLAMP

[76] Inventor: Keith Anthony Brinson, P.O. Box 410, Whigham, Ga. 31797

[21] Appl. No.: 680,604

[22] Filed: Jul. 16, 1996

[51] Int. Cl.$^6$ ................................................ A61B 17/28
[52] U.S. Cl. .................... 606/105; 606/205; 606/207; 81/415
[58] Field of Search ................ 606/86, 87, 105, 606/122, 205–209, 51, 52; 81/300, 415, 427.5

[56] References Cited

U.S. PATENT DOCUMENTS

| | | | |
|---|---|---|---|
| D. 246,190 | 10/1977 | Hodge | D24/27 |
| 2,427,128 | 9/1947 | Ettinger | 606/86 |
| 2,583,896 | 1/1952 | Siebrandt | 606/86 |
| 2,631,585 | 3/1953 | Siebrandt | 606/86 |
| 2,642,871 | 5/1953 | Thuerig | 606/207 |
| 5,036,733 | 8/1991 | Tiholiz et al. | 76/119 |

FOREIGN PATENT DOCUMENTS 655-646-A   5/1986   Switzerland.
1695903-A1  12/1991  U.S.S.R..

*Primary Examiner*—Michael Buiz
*Assistant Examiner*—David O. Reip
*Attorney, Agent, or Firm*—Carnes, Cona and Dixon

[57] ABSTRACT

The present invention provides a surgical clamp which enables a surgical team to use a clamp and plate simultaneously. The surgical clamp of the present invention includes a scissors-like structure having a pair of shafts which are hingedly and pivotally secured to each other via a pivot point. Located at one end of each shaft is a handle for enabling the user to grasp and manipulate the device, while located at the second end of each shaft is a bone engaging member. The pivotal point is located in proximity to the handles so as to provide for an adequate amount of clearance to exist between the bone engaging means and the surgical team. For providing the adequate amount of clearance, the shafts extending between the pivotal point and the bone engaging member includes an arc shape. This unique shape widens the gap or space between the two shafts. The clamp device further includes a locking member for locking this device in a fixed and secured position.

17 Claims, 3 Drawing Sheets

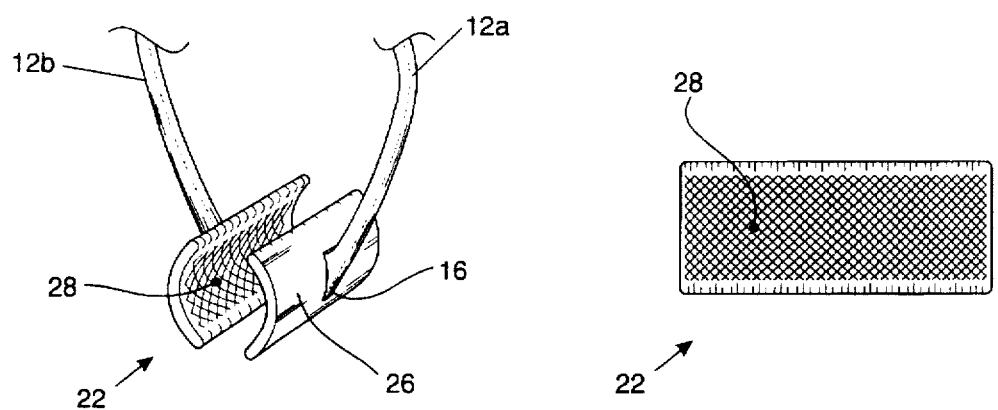
Figure 3
Figure 4
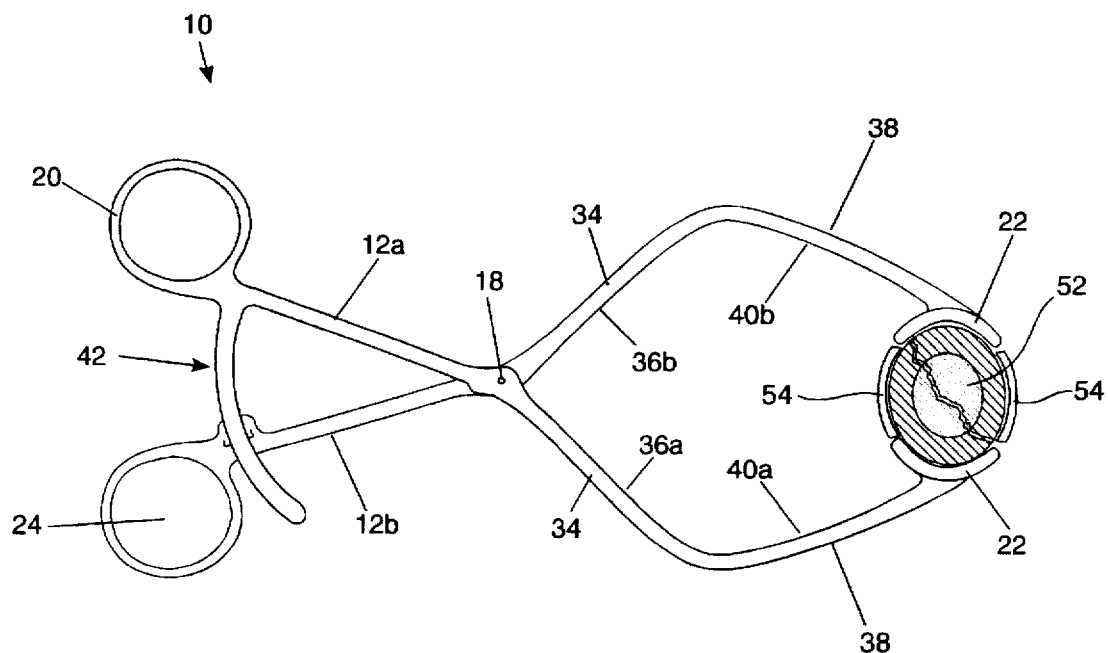
Figure 5

SURGICAL BONE CLAMP

BACKGROUND OF THE INVENTION

1. Field of the Invention

The present invention relates generally to surgical bone clamps and more particularly to a surgical bone clamp which is adapted to successfully maintain and align fragments of fractured bones during fixation of fractures or surgical osteotomies.

2. Description of the Prior Art

To adequately set broken bones, the bone fragments are properly aligned and a plate is secured thereto for bridging the fracture and enable proper healing. The plate is typically provided with a plurality of apertures. These apertures are adapted to receive and maintain screws. Proper alignment of the bone is of the utmost importance in order to achieve successful recovery.

Accordingly, during the surgical procedure, the plate is held against the fracture and a drill or the like is inserted into the apertures of the plate for rendering holes to be drilled into the bones. Screws are then inserted into the aperture for enabling the bone to be held in a fixed and secured position for providing proper alignment during the healing process.

To repair a fracture, the surgical team must first align the fracture by utilizing a conventional bone clamp. Once proper alignment is achieved the clamp is removed for placement of the plates. Several times the plates are not on accurately and the bones must be re-clamped, the clamp removed, and the plates placed on again. This process is continued until successful alignment is achieved. Successful alignment may take up to six or seven tries and can be painful to the patient. Another challenge associated with fixations of fractures or surgical osteotomies is holding a plate against the bone while drilling holes. Accordingly efforts have been made to aid and assist the surgeon during this tedious and at times cumbersome situation.

Such a device is disclosed in U.S. Pat. No. 2,427,128 issued to Ettinger, wherein there is disclosed a surgical clamp having a pair of handles which are pivotally attached for providing the clamp to have a pliers-like configuration. The clamp further includes a front including a means for grasping the bone and a back for enabling a user to hold and maintain the clamp. The means for grasping the bone includes an adjusting means for enabling the front to grasp any size bone. The back includes a means of locking the bone in a fixed and stable position. This device, though successful in maintaining an aligned fracture, is complex and cumbersome to use. Additionally, this device fails to provide adequate clearance for enabling a surgeon or the like to utilize a drill during a surgical procedure.

Yet another device is disclosed in U.S. Pat. No. 2,583,896 issued to Siebrandt. Siebrandt discloses a bone clamp device having a pair of pivotally attached handles and includes a front for grasping the bone and a back for enabling the user to maintain the clamp. The pivotal attachment occurs in proximity to the front of the clamp. This, unfortunately, provides an improper amount of clearance to exist between the clamp and the plate which will not enable a surgeon to properly utilize the drill. This device also includes a means for maintaining the bone in an aligned position as well as includes a means of maintaining and holding the plate in a fixed position. This additional means may be difficult and awkward to use while holding the clamp. The clamp is also provided with teeth for grasping and maintaining the fracture. If not properly secured, these teeth may cause more damage to the fracture.

Siebrandt discloses a second device or tool which is used in clamping a fracture. This tool is disclosed in U.S. Pat. No. 2,631,585. In this patent, Siebrandt utilizes a pair of bone clamps which are disposed in a parallel relationship. The bone clamps are connected via a turnbuckle which can be adjusted for altering the distance between the clamps. Each clamp includes a pair of pivotally attached handles having a front for grasping the bone and a back for enabling the user to maintain each clamp. The pivotal attachment occurs in proximity to the front of each clamp. This as well as the location of the turnbuckle, unfortunately, provides an improper amount of clearance to exist between the clamp and the plate which will not enable a surgeon to properly utilize the drill. Additionally, the use of two clamps and a turnbuckle provides a device which is difficult and awkward to use by a single individual, thereby inherently decreasing the efficiency of successfully using the tool.

Accordingly, there exists a need to provide for a clamp device which will be maintained on a plate efficiently and successfully during a surgical procedure. No previous efforts have been disclosed which provides the benefits intended with the present invention. None of these previous efforts, however, provide the benefits intended with the present invention. Additionally, prior techniques do not suggest the present inventive combination of component elements as disclosed and claimed herein. The present invention achieves its intended purposes, objectives and advantages over the prior art device through a new, useful and unobvious combination of component elements, which is simple to use, with the utilization of a minimum number of functioning parts, at a reasonable cost to manufacture, assemble, test and by employing only readily available material.

SUMMARY OF THE INVENTION

The present invention provides a clamp device which will enable a surgical team to use a clamp and plate simultaneously. The clamp device of the present invention will maintain the plate in a fixed and stable position so that the surgeon or the like can accurately drill holes in the appropriate locations via the openings within the plate.

The device of the present invention includes a scissors-like structure having a pair of shafts-like members which are hingedly and pivotally secured to each other via a pivot point. Located at one end of the shaft are handles for holding the device, while located oppositely from the handles is the bone engaging means. The pivotal point is located in proximity to the handles to provide for the length from the pivotal point to the bone engaging means to be sufficiently longer than the length from the handles to the pivotal point. This design and configuration will enable a sufficient amount of clearance to exist between the surgical team and the bone engaging means.

The bone engaging means is preferably curved to enable the bone engaging means to conform to the curved outer surfaces of any of the generally cylindrically shaped long bones in the body. This bone engaging means also includes a roughened surface so as to enable the bone to be maintained and secured within the bone engaging means.

For providing the clamp to be in a fixed and secured position, the clamping device can be equipped with a locking mechanism. This locking mechanism will allow the user to lock the shafts in a secured and fixed position.

Accordingly, it is the object of the present invention to provide for a bone clamp which will provide an efficient means of maintaining and securing a plate to the bone fragments for enabling the surgical team to simultaneously work on the bone while utilizing the clamp.

Still another object of the present invention is to provide for a bone clamp which will overcome the deficiencies, drawbacks and shortcomings of prior surgical bone clamp devices.

Yet another object of the present invention, to be specifically enumerated herein, is to provide a bone clamp in accordance with the preceding objects and which will conform to conventional forms of manufacture, be of simple construction and easy to use so as to provide a device that would be economically feasible, long lasting and relatively trouble free in operation.

Although there have been many inventions related to bone clamps, none of the inventions have become sufficiently compact and simple in design, easy to use, low cost, and reliable enough to become commonly used. The present invention meets the requirements of the simplified design, compact size, low initial cost, low operating cost, ease of installation and maintainability, and minimal amount of training to successfully employ the invention.

The foregoing has outlined some of the more pertinent objects of the invention. These objects should be construed to be merely illustrative of some of the more prominent features and application of the intended invention. Many other beneficial results can be obtained by applying the disclosed invention in a different manner or modifying the invention within the scope of the disclosure. Accordingly, a fuller understanding of the invention may be had by referring to the detailed description of the preferred embodiments in addition to the scope of the invention defined by the claims taken in conjunction with the accompanying drawings.

BRIEF DESCRIPTION OF THE DRAWINGS

FIG. 3 is a perspective view of the bone engaging means of the clamp device of the present invention.

FIG. 4 is a bottom planar view of the bone engaging means of the clamp device of the present invention.

FIG. 5 is a side planar view of the clamp device of the present invention secured to a bone.

Similar reference numerals refer to similar parts throughout the several views of the drawings.

DESCRIPTION OF THE PREFERRED EMBODIMENTS

Figure 1:
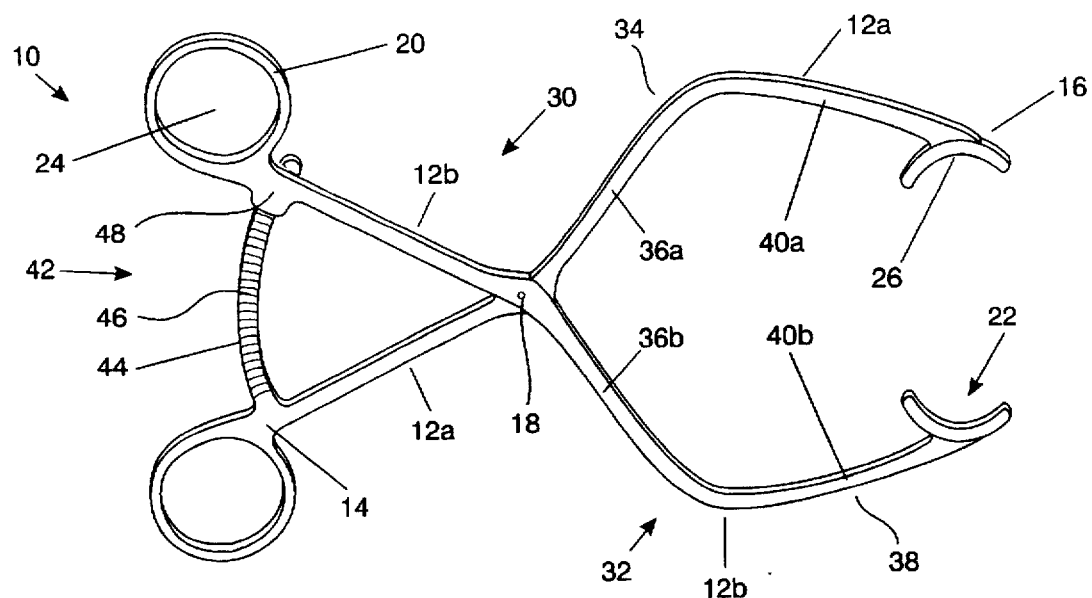
FIG. 1 is a front side planar view of the clamp device of the present invention.

As seen in the drawings, the clamp device 10 of the present invention includes a scissors-like structure. The clamp device 10 comprises a first shaft-like member 12a and a second shaft-like member 12b, each having opposite ends 14 and 16. These shaft-like members are pivotally secured at a pivot point 18, thereby providing for the scissors-like structure.

Located at the first end 14 of each shaft 12 is a handle 20. Located at the second end 16 of each shaft is a bone engaging means 22.

The handles 20 are used to hold the device as well as manipulate the bone engaging means around the fracture. As seen in the drawings, the handles are designed to have a circular or oval configuration having an opening 24 centrally located therein. The openings 24 are adapted to receive a thumb and index finger, respectively. The user is then able to maneuver the device using their thumb and index finger. This particular design will provide the user with a comfortable fit as well as an advantageous means for manipulating and handling the device 10.

Alternatively, for difficult and awkward fractures or circumstances, the shape and design of the handles 20 may allow the user to hold each handle with a different hand. In this mode of holding the device 10, the user will have their thumb located on the top surface of the handles while the four fingers will be located on the under surface of the handles. The circular or oval configuration permits for enough surface area to exist for rendering a comfortable fit on the handle for the user's hand. Due to the shape of the handles 20, the user can easily and comfortably grasp the handles as desired.

As seen in the drawings, the second end 16 of the shaft-like member is secured to the outer surface 26 of the bone engaging means 22. This securement can occur via any conventional means, such as the use of adhesives, welding, screws, or the like. Optionally, the shaft-like members can be integral with the bone engaging means 22.

Figure 6:
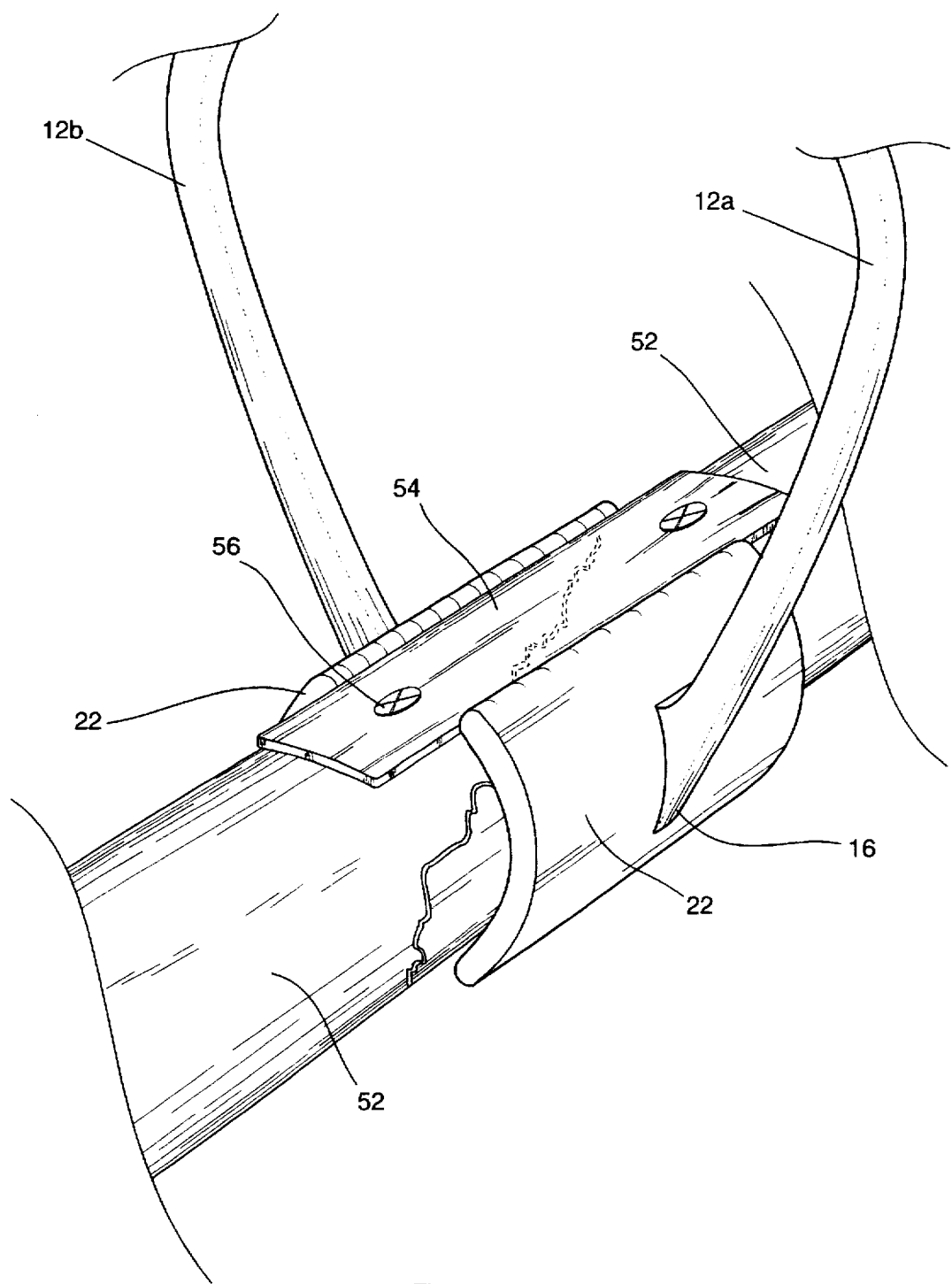
FIG. 6 is a partial perspective view of the clamp device of the present invention secured to a bone and engaging a plate to be affixed to the fracture.

Since the bone engaging means 22 is adapted to receive a bone 52, it is preferably designed and configured to be curved. Thereby, the inner surface 28 of the bone engaging means is curved inwardly. Additionally, as seen in FIGS. 3 and 6, the bone engaging means has a generally elongated and curved structure that is larger in width than the shaft-like members 12a or 12b. This will enable the bone engaging means to grasp and maintain the bone while the shaft-like members do not interfere with the health care provider working on the injured site. The enlarged width will also permit for the clamp device 10 to cover and maintain a larger area of the injured site.

For maintaining the clamp 10 in a fixed and secured position on the bone, the inner surface 28 of the clamp is roughened to provide for the inner surface to have a high coefficient of friction. This roughened surface is illustrated in FIG. 3. Alternatively, this inner surface 28 can be coated with a material having a high coefficient of friction. The roughened surface or the material will provide for the inner surface 28 to be highly resistive to movement. Inherently securing the bone engaging means 22 to the injured site in a fixed and secured position.

The shaft-like members 12a and 12b have a unique design and configuration. As seen in the drawings, the shaft-like members each include a back section 30 and a front section 32. The back section 30 encompasses the handles while the front section 32 encompasses the bone engaging means. The pivot point 18 divides the back section 30 from the front section 32.

The back section 30 is shorter in length than the front section 32. This provides for the pivot point to be located in proximity to the handles 20 of the clamp device 10. Providing for the pivot point 18 to be located in proximity to the back section 30 renders a sufficient amount of space to exist between the clamp device 10 and the injured site. The surgical team is adapted to work on the injured site while the clamp device is secured to the injured site.

The front section 32 of the clamp device 10 is designed to allow for enough clearance to exist between the clamp and the plate placed on the injured site. For permitting the proper clearance, the front section 32 of the clamp includes a unique design. As seen in the drawings, the front section 32 of the clamp includes a first portion 34 which extends outwardly from the pivot point 18. This will provide for the first part 36a of the first shaft-like member 12a to extend oppositely from the first part 36b of the second shaft-like member 12b.

Figure 2:
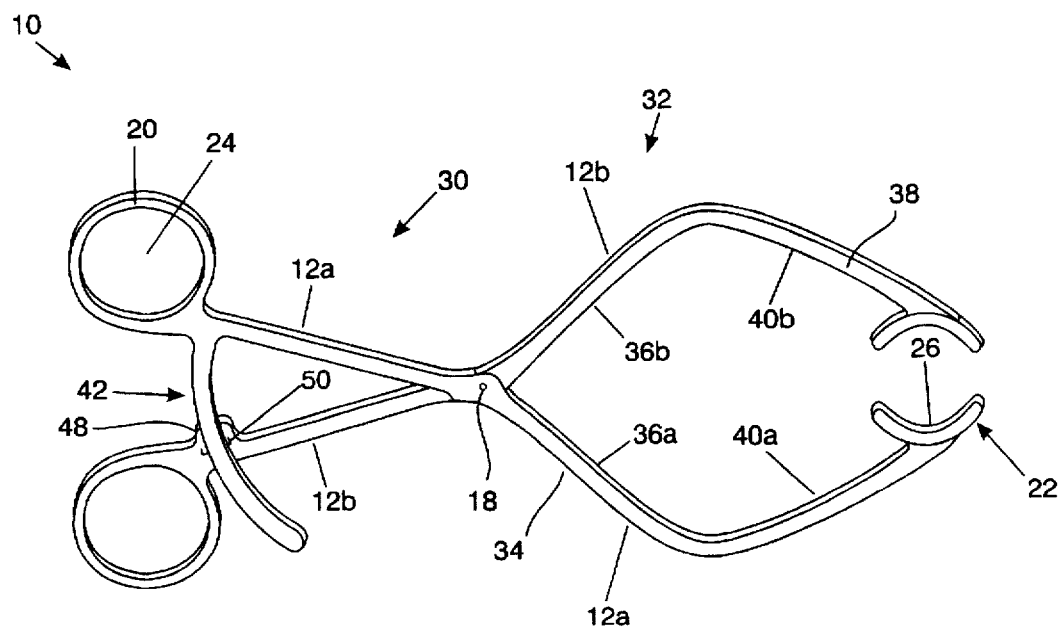
FIG. 2 is a back side planar view of the clamp of the present invention illustrating the locking mechanism.

The front section 32 of the clamp further includes a second portion 38 which extends inwardly from the first portion 34. This will provide for a second part 40a of the first shaft-like member 12a to extend inwardly from the first part 36a. A second part 40b of the second shaft-like member 12b extends inwardly from the first part 36b. This will provide for the second part 40a of the first shaft-like member 12a to extend towards the second part 40b of the second shaft-like member 12b. This will provide for the front portion 36 to have a diamond-like configuration. The diamond-like configuration will enable a significant amount of clearance to exist between the injured site and the clamp device, so as to allow a surgeon or the like to operate on the bone while the clamp is securely affixed onto the injured site. As seen in the drawings, particularly FIGS. 2 and 5, the highest point of the shaft members 12a and 12b is substantially aligned horizontally with the handles of the device 10, when the device is in a closed position. The handles, as seen, are the highest point of the back portion. This will allow for enough clearance to properly work on the injured site, as seen in FIG. 6. The highest point of each shaft member, as seen in the figures, is the point of contact between the first part 36a, 36b and the second part 40a, 40b, respectively.

To aid in securing the clamp to the injured site, the clamp device 10 includes a locking mechanism 42. The locking mechanism extends across the back section 30 and is located in proximity to the handles 20. This will provide for easy accessibility for the user. The locking mechanism 42 comprises a first member 44, having a plurality of teeth 46 which extends downwardly in a first direction. This first member 44 extends outwardly from the first end of the first shaft-like member 12a. The first member 44 is slightly arched.

Located on the first end 14 of the second shaft-like member is a second member 48. This second member 48 is adapted to engage the first member 42 of the locking mechanism 42, thereby providing for the first member to be removably secured to the second member. The second member 48 comprises of at least one tooth member 50 which extends downwardly in a second direction. The second direction is opposite from first direction. This will permit for the first section 44 to engage and lock with the second section 48.

Accordingly, to utilize the clamp device 10 of the present invention, the user grasps the handles 20. Manipulating the device via the handles 20, the user grasps the injured site of the bone 52 via the grasping means 22. As seen in FIGS. 5 and 6, once the bones are aligned, the user locks the clamping device in a fixed and secured position via the locking mechanism 42. When the fracture is aligned, the clamp secured, the surgeon or the like places the plates 54 on the injured site. The surgical team can then drill the appropriate holes via the apertures within the plate for enabling screws 56 to be inserted therein, allowing the first attempt to successfully achieve proper alignment.

While the invention has been particularly shown and described with reference to an embodiment thereof, it will be understood by those skilled in the art that various changes in form and detail may be made without departing from the spirit and scope of the invention.

I claim:

1. A surgical bone clamp comprising:
   a first shaft member and a second shaft member each having a first end, a second end, a back section and a front section;
   a bone engaging means secured to said second end of each of said first shaft member and said second shaft member, each of said bone engaging means comprising an elongated curved surface, said curved surface being shaped and configured to generally conform to and clamp around a curved outer surface of a long bone;
   said first shaft member is pivotally mounted said second shaft member at a pivot point and said pivot point is located in proximity to said first end of said first shaft member and said second shaft member;
   said front section of each of said first and second shaft members encompasses the bone engaging means and said back section of each of said first and second shaft members encompasses said first end;
   said pivot point divides said front section from said back section; and
   said back section is shorter in length than said front section;
   wherein said front section of said first shaft member and said front section of said second shaft member are each bent outwardly to form opposed arches, said opposed arches forming a substantially diamond-shaped opening when said clamp is in a fully closed position.

2. A surgical bone clamp as in claim 1 wherein said first end of said first shaft member and said first end of said second shaft member each include a handle.

3. A surgical bone clamp as in claim 2 wherein said handle is circular in shape and includes an opening located therein for receiving a thumb and index finger of a user.

4. A surgical bone clamp as in claim 2 wherein said handle is oval in shape and includes an opening located therein for receiving a thumb and index finger of a user.

5. A surgical bone clamp as in claim 1 wherein bone engaging means includes an inner surface and an outer surface, said second end of said first shaft member and said second end of said second shaft member is secured to said outer surface of said bone engaging means, and said inner surface is roughened for providing said inner surface to have a high coefficient of friction.

6. A surgical bone clamp as in claim 1 wherein bone engaging means includes an inner surface and an outer surface, said second end of said first shaft member and said second end of said second shaft member is secured to said outer surface of said bone engaging means, and said inner surface is coated with a material having a high coefficient of friction.

7. A surgical bone clamp as in claim 1 wherein said bone engaging means has a width and said width is wider than said second end of said first shaft member and said second end of said second shaft member.

8. A surgical bone clamp as in claim 1 wherein said front section of said first shaft member includes a first portion which extends outwardly and upwardly from said pivot point and said front section of said second shaft member includes a first portion which extends outwardly and downwardly from said pivot point, said first portion of said first shaft member extends oppositely from said first portion of said second shaft member, a second portion extends inwardly from said first portion of said first shaft member and a second portion extends upwardly from said first portion of said second shaft member, and said second portion of said first shaft member and said second portion of said second shaft member extend towards each other.

9. A surgical bone clamp as in claim 1 wherein a locking mechanism is located at said back section of said first shaft member and said second shaft member for locking said front section of said first shaft member and said second shaft member in a fixed and secure position.

10. A surgical bone clamp as in claim 9 wherein said first end of said first shaft member and said first end of said second shaft member each include a handle.

11. A surgical bone clamp as in claim 10 wherein said handle is circular or oval in shape and includes an opening located therein for receiving a thumb and index finger of a user.

12. A surgical bone clamp as in claim 10 wherein bone engaging means includes an inner surface and an outer surface, said second end of said first shaft member and said second end of said second shaft member is secured to said outer surface of said bone engaging means, and said inner surface is roughened for providing said inner surface to have a high coefficient of friction.

13. A surgical bone clamp as in claim 10 wherein bone engaging means includes an inner surface and an outer surface, said second end of said first shaft member and said second end of said second shaft member is secured to said outer surface of said bone engaging means, and said inner surface is coated with a material having a high coefficient of friction.

14. A surgical bone clamp as in claim 10 wherein said bone engaging means has a width and said width is wider than said second end of said first shaft member and said second end of said second shaft member.

15. A surgical bone clamp as in claim 1 wherein said front section of said first shaft member includes a first portion which extends outwardly and upwardly from said pivot point and said front section of said second shaft member includes a first portion which extends outwardly and downwardly from said pivot point, said first portion of said first shaft member extends oppositely from said first portion of said second shaft member, a second portion extends inwardly from said first portion of said first shaft member and a second portion extends upwardly from said first portion of said second shaft member, and said second portion of said first shaft member and said second portion of said second shaft member extend towards each other.

16. A surgical bone clamp comprising:

a first shaft member and a second shaft member each having a first end, a second end, a back section and a front section;

a bone engaging means secured to said second end of each of said first shaft member and second shaft member, each of said bone engaging means comprising an elongated curved surface, said curved surface being shaped and configured to generally conform to and clamp around a curved outer surface of a long bone;

said first shaft member is pivotally mounted to said second shaft member at a pivot point and said pivot point is located in proximity to said first end of said first shaft member and said second shaft member;

said front section of each of said first and second shaft members encompasses the bone engaging means and said back section of each of said first and second shaft members encompasses said first end; and said pivot point divides said front section from said back section;

wherein said front section of said first shaft member and said front section of said second shaft member are each bent outwardly to form opposed arches, said opposed arches forming a substantially diamond-shaped opening when said clamp is in a fully closed position.

17. A surgical bone clamp as in claim 16, wherein said back section is shorter in length than said front section.

* * * * *